United States Patent [19]
Korpman

[11] Patent Number: 5,681,305
[45] Date of Patent: Oct. 28, 1997

[54] MOLTEN ADHESIVE FIBERS AND PRODUCTS MADE THEREFROM

[75] Inventor: Ralf Korpman, Bridgewater, N.J.

[73] Assignee: McNeil-PPC, Inc., Skillman, N.J.

[21] Appl. No.: 442,270

[22] Filed: May 16, 1995

Related U.S. Application Data

[62] Division of Ser. No. 168,550, Dec. 16, 1993, Pat. No. 5,462,538.

[51] Int. Cl.$^6$ .............................. A61F 13/15; A61F 13/20
[52] U.S. Cl. ..................... 604/390; 604/370; 604/372; 604/386; 604/389; 604/359
[58] Field of Search ............................ 604/370, 372, 604/386, 389, 390, 359; 602/54; 524/270–272, 274; 428/214, 295, 30.5, 317.7, 355

[56] References Cited

U.S. PATENT DOCUMENTS

| | | | |
|---|---|---|---|
| 4,023,571 | 5/1977 | Comerford et al. | 604/386 |
| 4,047,534 | 9/1977 | Thomaschefsky | 604/380 |
| 5,114,781 | 5/1992 | Morman | 428/198 |

*Primary Examiner*—P. Zuttarelli

[57] ABSTRACT

Absorbent products and components for use in absorbent products are disclosed. These absorbent products comprise pressure-sensitive adhesive microfibers and thermoplastic polymer microfibers, that when incorporated into absorbent products provide good liquid transport properties, resiliency, and attachment systems; and further mask odors associated with bodily fluids.

6 Claims, 2 Drawing Sheets

MOLTEN ADHESIVE FIBERS AND PRODUCTS MADE THEREFROM

This is a division, of application Ser. No. 08/168,550, filed Dec. 16, 1993, now U.S. Pat. No. 5,462,538 which is hereby incorporated by reference.

FIELD OF THE INVENTION

This invention relates to absorbent products and absorbent materials useful in the manufacture of absorbent products, such as sanitary napkins, pantyliners, incontinence devices, diapers, and to such related absorbent products.

BACKGROUND OF THE INVENTION

Absorbent products such as sanitary napkins and diapers typically comprise an absorbent core, a liquid impermeable backing material, and a liquid permeable facing material. The impermeable backing material prevents the bodily fluid from seeping out from the absorbent core and staining the wearer's clothing. The absorbent core is also covered with a facing material that, inter alia, also serves to contain the absorbent core.

Normally, absorbent articles, such as pantyliners, sanitary napkins, baby and adult diapers, as well as other adult incontinence devices, are formed by securing a liquid impermeable film to an absorbent core and then attaching a facing material to the impermeable film thereby securing the absorbent core between these two layers. See, e.g., Datta, et al., U.S. Pat. No. 4,892,534, the disclosures of which are herein incorporated by reference in their entirety. This process is both time consuming and expensive. Moreover, if the facing is not in intimate contact with the core, the liquid on the surface of the facing will puddle up and not penetrate through the facing but rather run off the surface. This is highly undesirable behavior.

It is also undesirable to have the absorbent products move during use. The attachment systems presently available often fail in this regard. During storage, the attachment system's adhesive is covered with a release liner. Polyethylene or silicone coated polyethylene paper is frequently used on the liners. Current adhesive attachment systems consist of continuous coating of pressure-sensitive adhesives and a continuous silicone coating on a release liner. Adhesives are normally thermoplastic rubber based and hot melt coated, and are typically plasticized with oil. For various reasons, the oil is an undesirable component of the adhesive. It imparts poor holding properties to the adhesive and tends to move in the system by migrating from the adhesive to the film, which is quite undesirable. The release liner on the attachment adhesive is normally silicone or polyethylene coated paper. The resulting surface finish of silicone coated papers is super smooth and the adhesive contact is 100% with the release surface, which can be problematic. Depending on the type of silicone coating, the silicone release system may cause the adhesive to be too easily released or too difficult to release, which is undesirable. Thus, it is important that the release paper have optimum release properties and at the same time make effective contact with the adhesive.

Many absorbent products optionally contain liquid absorbers, or odor absorbing materials to mask the potential odor associated with the excreted bodily fluids. It has been very difficult to immobilize such absorbents in disposable products. Frequently the powder moves, which is very undesirable. In the past powders have been immobilized on foams, or on continually coated pressure-sensitive adhesive surfaces to adhere absorbent powder, and then inserted into the absorbent product. However, these approaches are expensive because a great quantity of adhesive is required for immobilizing such materials.

Despite the advances that have been made in the field of absorbent products such as sanitary napkins, pantyliners, diapers, and incontinence products, there are still needs to be addressed. For example, there is a need for absorbent products that have better liquid transport properties and better odor and liquid absorbing properties. There is a further need for absorbent products with more effective attachment systems to give the user more security that the product will remain in place during routine use. There is also a need for absorbent products that are manufactured using less expensive and more efficient techniques. The present invention addresses these, as well as other needs in the art.

SUMMARY OF THE INVENTION

The present invention utilizes microfiber technology to provide absorbent products that have good liquid transport properties, good liquid and odor absorbing properties, good attachment systems, and at the same time are produced efficiently and cost effectively. The microfibers of the invention comprise pressure-sensitive adhesives and/or plastic polymers, depending on the purpose the microfiber coating is to serve.

In general, the invention relates to a variety of substrates coated with microfibers, either pressure-sensitive adhesive microfibers or plastic polymer microfibers, at a weight in the range of about 0.05 to 2 ounces/square yard; the weight typically depends on the particular substrate, the particular microfibers, and the particular use of the substrate.

The pressure-sensitive adhesive microfibers may be coated onto substrates, such as a facing, backing, or absorbent product to improve the absorbent products' liquid transport properties, impart good liquid and odor absorbing properties, and good attachment systems. Pressure-sensitive adhesives generally comprise an elastomeric component, which comprises a linear or radial A-B-A block copolymer and a simple A-B block copolymer or combinations thereof, wherein said A blocks are derived from styrene and said B blocks are derived from alkenes or dienes; a resin component that comprises a solid or liquid tackifier; and optionally a plasticizer.

The plastic polymer microfibers are used, inter alia, for forming absorbent articles in situ or for forming release liners with enhanced release properties. These plastic polymers are selected from the group consisting of polyethylene, polypropylene, ethylene vinylacetate, copolyesters, and plastic or thermoplastic rubber alloys.

In various embodiments, the microfibers typically have an average diameter of less than about 100 microns; however, this parameter also depends on the substrate, the microfibers, and the particular use the microfiber coating is to serve. The substrate may be an apertured, liquid permeable film; a liquid impermeable backing; an absorbent panel or core; or an absorbent product. Many of the pressure-sensitive adhesive microfiber coated substrates and plastic polymer microfiber coated substrates of the invention may be used as components in a wide variety of absorbent products such as sanitary napkins, pantyliners, incontinence devices, and diapers, without limitation. For example, the attachment systems, components with enhanced liquid transport properties, and the odor and liquid absorbing components disclosed herein have general application to absorbent articles. Each of these embodiments, as well as others, are discussed below.

In one embodiment of the invention, absorbent components having enhanced liquid transport properties are presented. These components may be incorporated into a wide variety of absorbent products. These components typically comprise a liquid permeable facing material coated with pressure-sensitive adhesive microfibers. The coated facing material is then placed adjacent to an absorbent core, with the coated side adjacent to the core. The coating of pressure-sensitive microfibers enhances liquid transport properties by placing the facing and absorbent core in intimate contact with each other. Products incorporating these components may further comprise a liquid impermeable backing.

In another embodiment of the invention, pressure-sensitive adhesive microfibers may be used to prepare liquid or odor absorbing components that may be incorporated into a variety of absorbent products. Components such as a facing or backing material or an absorbent core are coated with pressure-sensitive adhesive microfibers. The pressure-sensitive adhesive microfibers are further coated with a liquid or odor absorbent.

In another embodiment of the invention, systems for attaching absorbent products to a wearer's garment are disclosed. The attachment systems of the invention comprise a substrate that is coated with pressure-sensitive adhesive microfibers on the side of the substrate that faces the garment, and a release paper that protects the pressure-sensitive adhesive coating up until the time the product is used. These attachment systems may be used in a variety of absorbent products.

Another aspect of the invention relates to forming absorbent products in situ. These absorbent products have plastic polymer microfiber coatings in place of standard liquid permeable covers and/or liquid impermeable backings—that is, the facing and backing can be formed in situ. For example, an absorbent core may be coated with plastic polymer microfibers on the body-facing side of the absorbent core thereby forming a liquid permeable facing over the core. In another example, an absorbent core may be sprayed on both sides with plastic polymer microfibers, forming a liquid permeable facing surface on one side of the absorbent core and a liquid impermeable backing surface on the opposite side of the absorbent core.

The invention further embodies absorbent products for adhesive attachment to a wearer's garment incorporating the aforementioned components. Such absorbent products comprise a liquid impermeable backing, which may optionally be coated with pressure-sensitive adhesive microfibers, and optionally have a liquid or odor absorbent immobilized on it; a liquid permeable facing, which may optionally be coated with pressure-sensitive adhesive microfibers, and optionally have a liquid or odor absorbent immobilized on it; an absorbent core fixed between the facing and backing, which may optionally be coated with pressure-sensitive adhesive microfibers, and optionally have a liquid or odor absorbent immobilized on it; pressure-sensitive microfiber adhesive coating on the body-facing surface of the backing that is contacted with the wearer's garment; and a release paper covering over the pressure-sensitive adhesive.

DETAILED DESCRIPTION OF THE PREFERRED EMBODIMENTS

Figure 1:
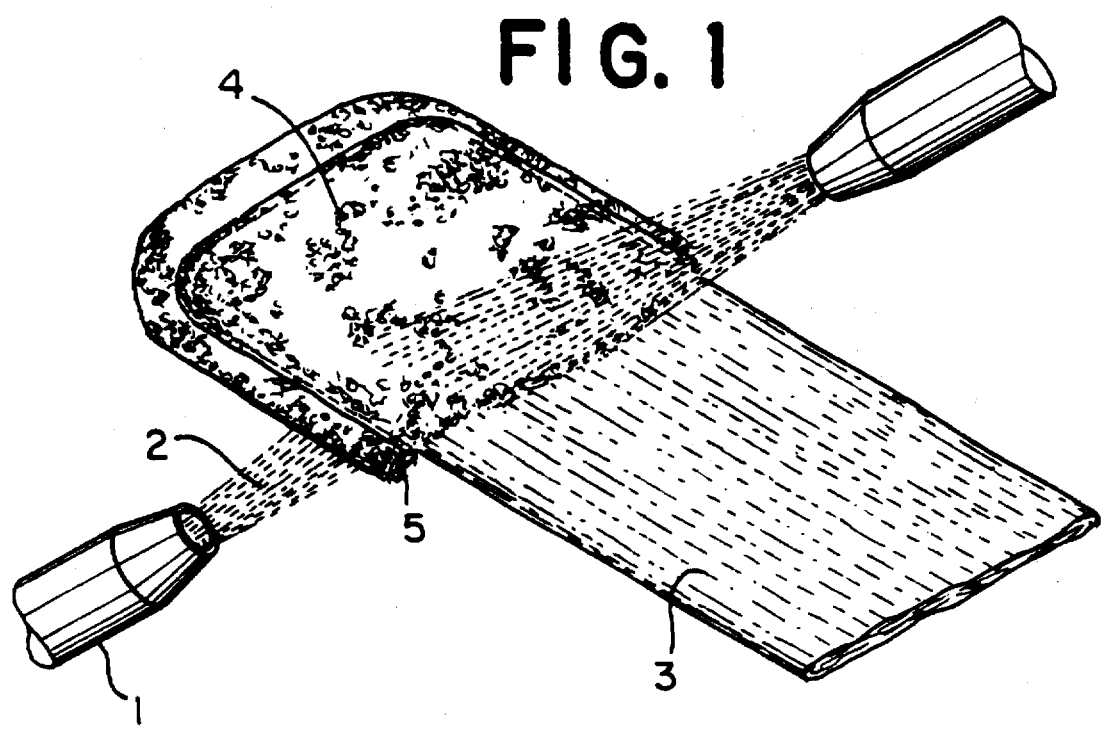
FIG. 1 depicts a top and bottom view of an absorbent product that is formed in situ. The absorbent core 3 is being coated with microfibers 2 on the top surface, the surface that faces the user's body 4, using a spray nozzle 1 to form the liquid permeable facing. Fibers are also being sprayed on the bottom 5, the surface facing the wearer's garment, to form the liquid impermeable backing 5. The fibers are being sprayed onto the core's top and bottom surfaces using a nozzle 1. The spray nozzle method is only one method of spraying microfibers onto substrates. The fibers sprayed using this method are typically spiral. Another method for spraying microfibers is the melt-blown die technique, which sprays the microfibers straight; this technique is preferable.

The present invention presents absorbent components, absorbent products, and materials utilizing microfibers of pressure-sensitive adhesives and/or plastic polymers. These pressure-sensitive adhesive and plastic polymer microfibers are formed using molten spray technology. The resulting microfibers can be incorporated, inter alia, into absorbent articles to enhance liquid transport properties, enhance liquid and odor absorbing properties, and provide good attachment systems. The use of these pressure-sensitive adhesives and plastic polymer microfibers produce absorbent products more efficiently and economically than available methods.

In the context of this invention, the term "substrate" refers to any material that can receive the pressure-sensitive adhesive or plastic polymer microfibers in accordance with the invention; for example, a facing material, backing material, absorbent core, or absorbent product, without limitation. As used herein, the terminology "facing material" means that liquid-permeable component of the absorbent product that is in contact with the user's skin when in use and covers at least one side of the absorbent core. The terminology "backing material" means, as used herein, that portion of the absorbent product that comes in contact with the wearer's clothing and covers at least one side of the absorbent core. In the context of the invention, the terms "absorbent core" or "absorbent panel" are used interchangeably, and mean that component of the absorbent product fixed between the facing and backing materials to absorb bodily fluid. The terminology "liquid absorbent," "odor absorbent," and "super absorbent" refers to any material that is capable of absorbing liquid or odor. In the context of this invention, a "plasticizer" means any material that gives an otherwise rigid material, such as plastic, flexibility. Typically, plasticizers are used in pressure-sensitive adhesives to give such adhesives wetness or tackiness. As used herein "elastomeric" refers to thermoplastic materials that can be linear, radial, or branched molecular structures that will repeatedly soften when heated and solidify when cooled, such as acrylics, polyethylenes, polypropylenes, nylons, and thermoplastic rubbers as styrene or isoprene and are a component of the pressure-sensitive adhesives of the invention. In the context of this invention, "resin" refers to any solid or liquid organic material of natural or synthetic origin that has an undefined melting point, and is generally a polymer. As used herein, the term "plastic polymers" refers to thermoplastic polymer materials such as polyethylene, polypropylene, ethylene vinylacetate, copolyesters, and rubber or plastic alloys, and are used in forming, inter alia, absorbent products in situ and release liners. The term "microfibers," as used herein, refers collectively to microfibers of pressure-sensitive adhesives and/or thermoplastics, unless otherwise specified.

Fiberized pressure-sensitive adhesives and plastic polymers can be applied in hot melt form using a spray fiberization method to form absorbent components and products with good attachment properties, good liquid transport properties, and good odor and liquid absorbing properties. Equipment is known in the art for forming microfibers—the microfiber nozzle spray (see FIGS. 1 and 2) or the melt blown die fiber formation process. Both of these systems produce small diameter fibers having an average diameter not greater than about 100 microns, the melt blown die process is preferred. In both systems the molten microfibers are extruded through a microspray nozzle or through a plurality of circular capillaries as filaments which are then processed through a low or high velocity gas (i.e., air) stream that attenuates the filaments of molten microfibers to reduce their diameter to a desired range for use in components of absorbent products and absorbent products. These microfibers when still in a substantially molten state or after some cooling, depending on the microfibers and desired use, are deposited on a desired substrate and allowed to cool further.

The microfibers of the invention are employed in various manners in formulating absorbent articles and materials used as component parts of absorbent articles, but the microfibers generally preferably have certain properties. The materials preferably have a high melt index, at least above 100, and more preferably above 1000; thus requiring a low volume of air in the fiber making process. Such materials will be readily apparent to those skilled in the art once armed with the present disclosure and may be used without departing from the spirit of the invention. The microfibers are typically microsized, have an average diameter of less than about 100 microns so they do not interfere with liquid transport. Where it is desired that the microfibers not be affected by liquid, the microfibers will preferably be hydrophobic, (i.e., when used to form a liquid impermeable backing material). The microfiber compositions preferably have a high plasticity so that they do not flow out excessively once deposited on a substrate. The microfibers preferably have a reasonable strength and the pressure-sensitive adhesive microfibers, in particular, should have good adhesive properties.

Typically the plastic polymers are selected from the group consisting essentially of polyethylene, polypropylene, ethylene vinylacetate, copolyesters, and plastic or thermoplastic rubber alloys.

Typically the pressure-sensitive adhesives of the invention comprise an elastomeric component, a resin component, and optionally a plasticizer to enhance wetness and tackiness. Generally, the pressure-sensitive adhesives comprise linear or radial block copolymers (A-B-A), simple block copolymers (A-B), or combinations thereof. The A-blocks (end blocks) are derived, (i.e., polymerized), from styrene or styrene homologues, and the B-blocks (center blocks) are derived from conjugated dienes, such as isoprene or butadiene, or from lower alkenes, such as ethylene and butylene, and polymers and copolymers thereof. Preferably, these pressure-sensitive adhesives typically comprise styrene-isoprene-styrene (SIS) thermoplastic block copolymers having a low coupling efficiency (about 15–65%) and less than about 30% styrene.

In certain preferred embodiments, the pressure-sensitive adhesive microfibers will have styrene-isoprene (SI) in the elastomer, and are tackified with a solid or liquid resin, and may optionally be plasticized with a liquid resin or liquid rubber. Following is a discussion of preferred embodiments with all parts expressed in parts per one hundred parts by weight of the elastomeric component. The discussion of the pressure-sensitive adhesive microfibers presents two general compositions, which may have varying ratios of polymers. These two general compositions are for illustrative purposes and are not intended to limit the invention.

In certain compositions, the elastomeric component preferably comprises from about 10 to about 100 parts of a linear or radial A-B-A block copolymer and about 0 to about 90 parts of a simple A-B block copolymer, more preferably from about 15 to about 75 parts of a linear or radial A-B-A block copolymer and about 25 to about 85 parts of a simple A-B block copolymer, more preferably from about 35 to about 75 parts of a linear or radial A-B-A block copolymer and about 25 to about 65 parts of a simple A-B block copolymer, more preferably from about 50 to about 90 parts of a linear or radial A-B-A block copolymer and about 10 to about 50 parts of a simple A-B block copolymer, more preferably, the elastomeric component will comprises from about 60 to about 80 parts of a linear or radial A-B-A block copolymer and about 20 to about 40 parts of a simple A-B block copolymer, the A blocks in the A-B block copolymer comprise from about 5 to about 50% by weight of the A-B copolymer, more preferably between about 10 to about 40%, and more preferably between about 10 to about 35%; and the total A-B and A-B-A copolymers comprise less than about 50% styrene, more preferably less than about 40%, and more preferably less than about 30%; and the resin component comprises from about 20 to about 300 parts of a tackifier such as a solid or liquid resin or combinations for said elastomeric component, more preferably from about 100 to about 140 parts of a tackifier such as a solid or liquid resin or combinations thereof for said elastomeric component, more preferably 50 to 120 parts of a solid or liquid resin or combinations thereof.

In other preferred embodiments, the elastomeric component will comprise from about 15 to about 45 parts of a linear or radial A-B-A block copolymer and about 55 to about 85 parts of a simple A-B block copolymer, more preferably from about 60 to about 75 parts of the A-B block copolymer and about 25 to about 40 parts of the A-B-A block copolymer, the A blocks in the A-B block copolymer preferably constitute from about 5 to about 50% by weight of the A-B copolymer, more preferably from about 10 to about 30%, from about 5 to about 20%, more preferably from about 10 to about 18%, and more preferably from about 12 to about 16%.; and the total A-B and A-B-A copolymers comprise less than about 30% styrene, more preferably less than about 25%, and more preferably less than about 20%; and the resin component preferably will comprise from about 20 to about 300 parts of a tackifier such as a solid or liquid resin or combinations thereof, more preferably between about 40 to about 200, and more preferably 50 to 120 parts of a resin.

These and other pressure-sensitive adhesives suitable for practicing the claimed invention are set forth in U.S. Pat.

Nos. 4,136,071, 4,080,348, and 4,759,754 issued to Korpman on Jan. 23, 1979, Mar. 21, 1978, and Jul. 26, 1988, respectively, the disclosures of which are herein incorporated by reference in their entirety. Certain components of the pressure-sensitive adhesives that may be used in practicing certain specific aspects of the claimed invention are commercially available. For example, Kraton RD 6043 is an SIS (styrene-isoprene-styrene) thermoplastic rubber having a 42% coupling efficiency and 220,000 M.W., and 17% styrene and is available from the Shell Company. Kraton 1117 is a commercially available thermoplastic rubber having a 65% coupling efficiency and 17% styrene. Kraton 1117 is a polystyrene-polyisoprene-polystyrene thermoplastic elastomer sold by the Shell Company and is believed to comprise about 35 parts A-B and about 65 parts A-B-A. Other such pressure-sensitive adhesive materials will be readily apparent to those skilled in the art once armed with the present disclosure and may be used without departing from the spirit of the invention.

The resin component consists essentially of tackifier resins for the elastomeric component. In general any compatible conventional tackifier resin or mixture of such resins may be used. Suitable resins are any compatible conventional tackifier resins or mixtures thereof. These resins include, but are not limited to, hydrocarbon resins, rosin and rosin derivatives, and polyterpenes. Wingtack Plus, for example, is a commercially available resin. Wingtack Plus is a solid tackifier resin sold by Goodyear Tire and Rubber Company consisting predominantly of polymerized structures derived from piperylene and isoprene with a softening point of about 95° C. Other resins suitable for use as tackifiers will be readily apparent to those skilled in the art once armed with the present disclosure and may be used without departing from the spirit of the invention.

Plasticizers for pressure-sensitive adhesives include, but are not limited to, LIR 310, which is a liquid SI (styrene-isoprene) polymer available commercially from Arakawa Chemical Company. Wingtack 10 is a liquid hydrocarbon tackifier of resin believed to comprise synthetic polyterpene, and is used as a plasticizer for pressure-sensitive adhesives. It has a softening point of 10° C., a viscosity of 20–40,000 cps at room temperature and a molecular weight of about 450. It is available from Goodyear Chemical Company. Other plasticizers will be readily apparent to those skilled in the art and may be used without departing from the spirit of the invention.

Generally, the pressure-sensitive adhesive and the plastic polymer microfibers preferably have an average diameter of less than about 100 microns, more preferably less than about 50 microns, and in certain embodiments more preferably between about 0.5 to about 25 microns. The microfibers' coating weight is preferably less than about 2 ounces/square yard, in certain other embodiments more preferably about 0.75 ounces/square yard, in certain other embodiments more preferably between about 0.3 to about 0.6 ounces/square yard, in yet other embodiments more preferably between about 0.2 to about 0.3 ounces/square yard, and in certain other embodiments more preferably the coating has a weight of between about 0.05 to about 0.15 ounces/square yard. The particular variables are discussed below in connection with various embodiments. The choice of the microfibers, coating weight of the microfibers, and the diameter of the microfibers is typically dictated by the particular use of the microfiber compositions.

The microfiber compositions used in the various embodiments of the invention may also contain other materials, such as antioxidants, heat stabilizers, and ultraviolet absorbers. Antioxidants that may be incorporated into the compositions, in particular the pressure-sensitive adhesive compositions, include, but are not limited to, Sanotovar A, which is a trademark for 2,5 diteriaryl amyl hydroquinone, ditertiary butyl cresol, and Butyl Zimate, which is a trademark for zinc di-n-butyl-dithiocarbamate. Any others known to those skilled in the art may be used without departing from the spirit of the invention.

Fillers, such as zinc oxide, aluminum hydrate, clay, calcium carbonate, titanium dioxide, carbon black, and others may also be incorporated into the microfiber compositions, in particular the pressure-sensitive adhesive microfiber compositions, without departing from the spirit of the invention. The various embodiments using pressure-sensitive adhesive microfibers and/or plastic polymer microfibers are presented below.

In general, one aspect of the invention presents a substrate coated on at least one surface with pressure-sensitive adhesive microfibers at a weight in the range of about 0.05 to about 2 ounces/square yard wherein said pressure-sensitive adhesive microfibers comprise an elastomeric component, a resin component, and optionally a plasticizer; and said microfibers have an average diameter of less than about 100 microns. Preferably, the elastomeric component comprises a linear or radial A-B-A block copolymer and a simple A-B block copolymer, wherein said A blocks are derived from styrene or styrene homologues and said B blocks are derived from alkenes or dienes. The polymers of the elastomeric component and their ratios have been discussed above; the resin component and its ratio in the pressure-sensitive adhesive has also been discussed above.

In one more specific embodiment, the substrate is a liquid permeable facing material 10. The facing material 10 is coated with pressure-sensitive adhesive microfibers on the side to be contacted with the core 12. These microfibers have a weight from about 0.05 to about 0.4 ounces/square yard; preferably the coating weight is about 0.25 ounces/square yard, more preferably about 0.18 ounces/square yard, and more preferably about 0.10 ounces/square yard. The average diameter of the pressure-sensitive adhesive microfibers is less than about 50 microns, more preferably between about 1 to about 25 microns.

A facing material 10 coated with a layer of pressure-sensitive adhesive microfibers can be used to produce an absorbent product with enhanced liquid transport properties. The pressure-sensitive adhesive microfiber coated surface (underside of 10) of the facing material 10 is placed adjacent to an absorbent core 12 or panel, and the adhesive fibers serve to maintain the facing in intimate contact with the core while not obstructing passage of fluid through the facing to the core 12. This structure allows the instantaneous transportation of liquids from the surface of the facing material into the absorbent panel, leaving a substantially dry surface on the body-facing surface of the facing material. This is highly desirable because the user is then protected from the liquid caused by bodily exudate.

The coated liquid permeable facing material is incorporated into an absorbent product using techniques known in the art. For example, the pressure-sensitive adhesive coated side of the liquid permeable facing material is placed adjacent to the absorbent core so that the two are in intimate contact, and then the outer rim of the facing material is secured to the core. Any methods known to those skilled in the art for accomplishing this contact may be used without departing from the spirit of the invention.

Absorbent cores suitable for use with this invention may be formed from both absorbent pulp fibers and resilient, synthetic fibers. The pulp fibers are generally formed from fiberizing wood pulp sheets and generally comprise a combination of long and short fibers. Suitable resilient, synthetic fibers include, but are not limited to, polyester and polyethylene fibers. The relative amounts of pulp fibers and synthetic fibers are not critical and can be determined by one skilled in designing such products, in an effort to balance and achieve the desired properties of absorbency and resiliency. The wood pulp fibers and synthetic fibers may be blended homogeneously throughout the absorbent core, or the relative proportions of each may vary throughout the absorbent core.

Absorbent cores may also be formed by other known techniques in which the fibers, pulp and/or synthetic, are airlaid. To form the most stable core, the fibers in the core are preferably bonded to one another. This may be done by heating the core to a temperature above the melting temperature of the synthetic fibers so those fibers fuse and bond to one another. Alternatively, bonding agents such as different thermo-bonding fibers, hot melt spray adhesives, and bonding powders may be utilized. Specific means that can be used to bond the fibers together include convection ovens, di-electric ovens (radio frequency and microwave), infrared ovens, heated calendar rolls, forced hot-air ovens, forced hot air during the panel forming process, and spray hot melt adhesive during the panel forming process.

The liquid permeable facing provided on the absorbent structure of the present invention should preferably be a film or fabric having a high degree of moisture permeability. For example, the fabric may be polyester, polyethylene, polypropylene, bicomponent fiber, nylon, rayon, or the like. The most suitable fabrics have unusually high elongation, loft, softness and drape characteristics. Films that are perforated or noncontinuous are also satisfactory. Though the cover is moisture permeable, it is preferably of the type which after permeation of the moisture, prevents strike-back of the body fluid when the absorbent structure is approaching saturation.

The liquid impermeable backing may be a liquid-impermeable polyolefin film, e.g., polyethylene or polyethylene terephthalate.

Figure 3:
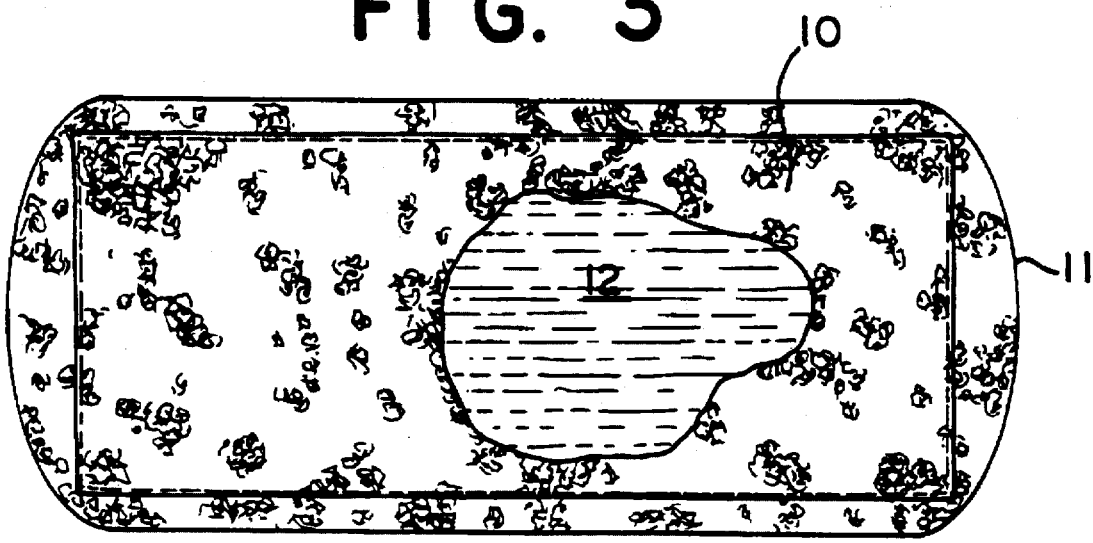
FIG. 3 depicts an absorbent product, sanitary napkin, with a portion cut away to show the core 12; the facing 10 and backing 11 are also depicted. The core 12 may be coated with microfibers as depicted in FIG. 1 before it is contacted with the facing 10. Alternatively, the facing 10 or backing 11 may be coated with microfibers before being contacted with the core 12. The microfibers sprayed on these various substrates may have a liquid or odor absorbent immobilized on it before the sanitary napkin is assembled.
Figure 4:
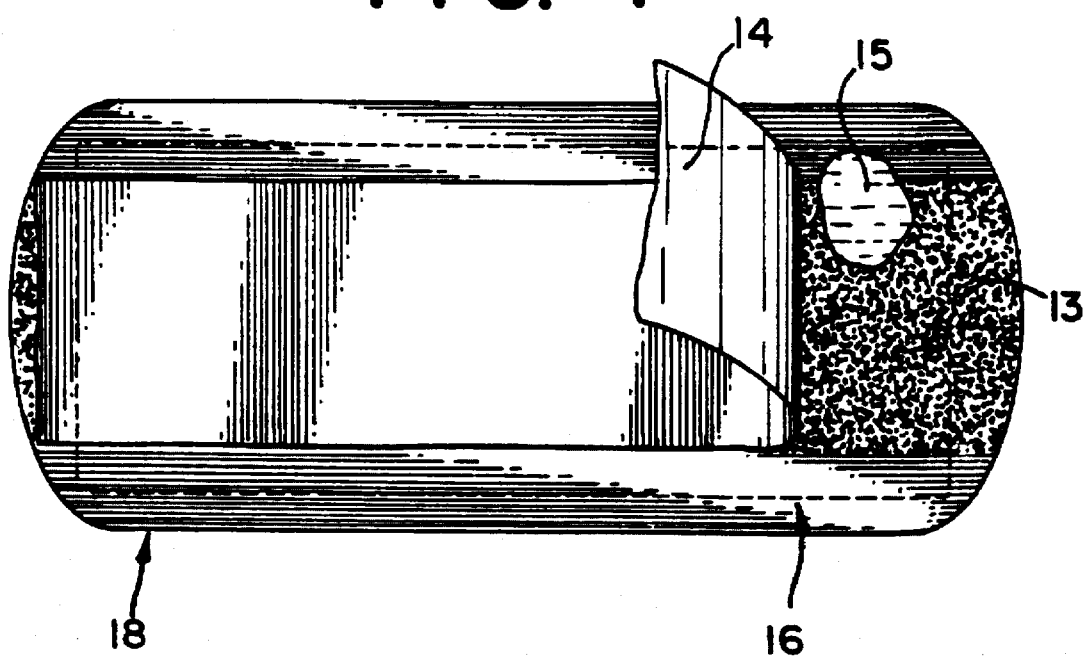
FIG. 4 illustrates a sanitary napkin and its various components. The absorbent core 15 is fixed between the facing 18 and the backing 16. The backing 16 is coated with adhesive microfibers 13 and then covered with a release paper 14.

In another specific embodiment, pressure-sensitive adhesive microfibers may also be used to immobilize liquid or odor absorbents on components of absorbent products, such as a facing 10 or backing 11 material, or absorbent core 12. These coated components may then be incorporated into absorbent products as depicted in FIGS. 3 and 4.

Heretofore, it has been difficult to immobilize particular liquid or odor absorbents on a substrate (i.e., a facing or backing material or an absorbent core) and then incorporate the substrate into absorbent products. Often these liquid or odor absorbers are powders that tend to move. The pressure-sensitive adhesives can prevent this movement. When used in this manner, the substrate receiving the pressure-sensitive adhesive microfibers may be an absorbent panel 12, facing material 10, or backing material 11. It is preferred that the coating weight be less than about 0.75 ounces/square yard, more preferably between about 0.35 ounces/square yard to about 0.6 ounces/square yard, and more preferably about 0.4 ounces/square yard. It is preferred that the average diameter of the pressure-sensitive adhesive microfibers be less than about 50 microns, more preferably between about 1 to about 25 microns. Absorbent products containing liquid or odor absorbents, as described above, may be made according to methods known to those skilled in the art without departing from the spirit of the invention.

Generally, an absorbent powder is immobilized on a pressure-sensitive adhesive coated facing material 10 before the side of the facing material coated with the pressure-sensitive adhesive (underside of 10) is contacted with an absorbent core 12.

The absorbent powders or liquids that may be incorporated into the absorbent products of the invention will be readily apparent to those skilled in the art. For example, superabsorbents are well known in the art. One type of superabsorbent material provides particles or fibers that may be described chemically as having a backbone of natural or synthetic polymers with hydrophilic groups or polymers containing hydrophilic groups being chemically bonded to the backbone or an intimate mixture therewith. Included in this class of materials are such modified natural and regenerated polymers as polysaccharides including, for example, cellulose and starch and regenerated cellulose which are modified by being carboxylalkylated, phosphonoalkylated, sulfoalkylated, or phosphorylated to render them highly hydrophilic. Such modified polymers may also be cross-linked to improve their water-insolubility. Odor control agents suitable for practicing this invention include, but are not limited to, baking soda and activated charcoal. Any other liquid or odor absorbent materials known to those skilled in the art may be used without departing from the spirit of the invention.

In another specific embodiment of the invention, the pressure-sensitive adhesive microfiber coating is used as part of an attachment system 13 and 14 for attaching absorbent products to the user's garment. The substrate to receive the coating 13 (see e.g., FIGS. 3 and 4) in this embodiment is an absorbent product (see FIG. 4); the side facing the user's garment will receive the coating. The coating 13 comprises pressure-sensitive adhesive microfibers having a coating weight of between about 0.2 to about 1 ounces/square yard, more preferably between about 0.2 to about 0.75 ounces/square yard, and more preferably about 0.25 ounces/square yard or less. The pressure-sensitive adhesive microfibers preferably have an average diameter of less than about 50 microns, more preferably less than 30 microns, and more preferably have an average diameter of between about 1 to about 25 microns. In preferred embodiments, the substrate is an absorbent product, preferably the pressure-sensitive adhesive microfiber coating 13 is on the garment facing surface of the absorbent product (see FIG. 4).

Figure 2:
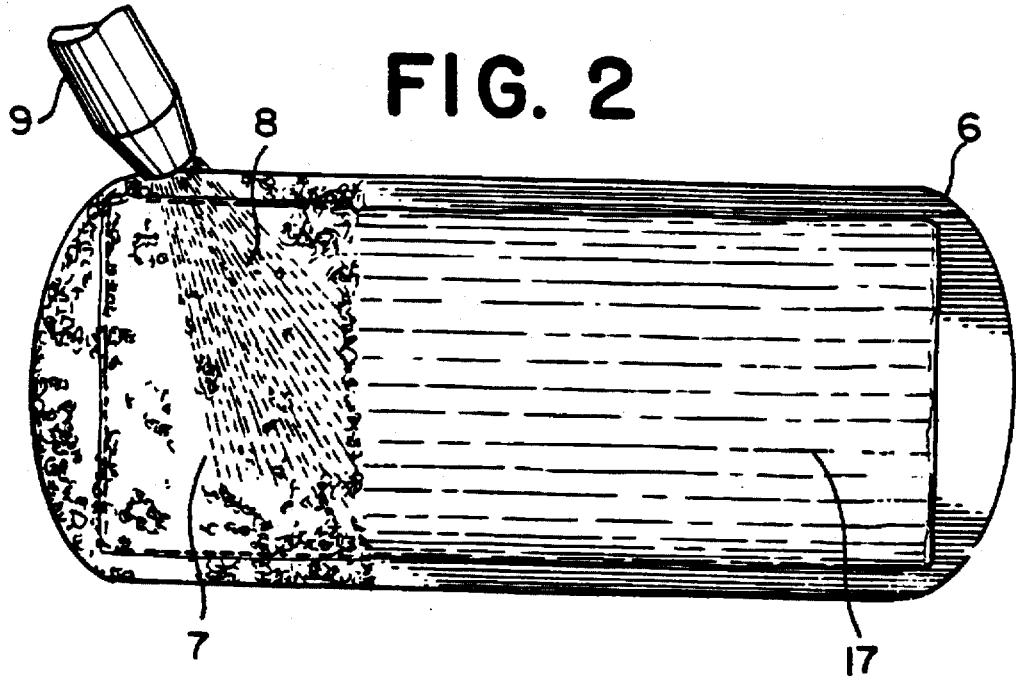
FIG. 2 depicts an absorbent core 17 with a liquid impermeable backing 6 secured to the core's 17 bottom side. The top of the core 17 is being coated 9 with microfibers 8 thereby forming a liquid permeable facing 7 on the side of the core opposite the backing 6.

In another aspect of the invention, absorbent products formed in situ using molten fiber spray technology are disclosed, rather than assembling the absorbent product from the individual components—facing, backing, and core (see FIGS. 1 and 2). In this aspect of the invention, the microfibers are plastic polymers. The plastic polymer microfibers may be sprayed 1 directly on an absorbent core 3, and may perform as a facing 4, backing 5, or both.

In one embodiment, only the facing fabric is eliminated (see FIG. 2). Generally, this approach requires that the absorbent core 17 be formed first and then contacted with a liquid impermeable barrier 6. The barrier 6, which may optionally be coated with pressure-sensitive adhesive microfibers before being contacted with the core 17, and optionally have a liquid or odor absorbent immobilized on it, is preferably laminated to one surface of the absorbent core 17 before a plastic polymer microfiber coating is placed on the opposite surface of the core 7. Methods for securing the backing to the core are known in the art and may be used without departing form the spirit of the invention. The facing material 7 is then sprayed 9 directly on the absorbent core 17 by spraying melt blown plastic-polymer microfibers 8 on the surface of the absorbent core 17 opposite the side that is in contact with the liquid impermeable barrier. In forming the facing side 7, plastic polymer hydrophilic microfibers or a very thin layer of hydrophobic microfibers 8 are sprayed onto the absorbent core 17, which will permit liquid strike-through and deliver a nearly dry cover. Here the plastic polymer microfibers should be cooled before coating the absorbent core.

In another embodiment of the invention, both the facing and the backing material are eliminated (see FIG. 1). Generally, the backing 5 is replaced with plastic polymer hydrophobic microfibers 2 sprayed 1 on the absorbent panel. The facing is formed as described above.

The plastic polymers used in forming absorbent products in situ are preferably selected from the group consisting of polyethylene, polypropylene, ethylene vinylacetate, copolyesters, and plastic or thermoplastic rubber alloys, with polyethylene preferred. The plastic polymer microfibers may be hydrophilic, hydrophobic, or combinations thereof depending on the intended purpose. In forming the facing, the molten microfibers should be cooled before being coated onto the substrate. The coating weight is preferably between about 0.2 to 1 ounces/square yard, more preferably between about 0.5 to 0.9 ounces/square yard, and more preferably about 0.6 to 0.8 ounces/square yard. If the fibers are hydrophobic, the coating weight should be between about 0.2 to about 0.75 ounces/square yard, more preferably between about 0.3 to about 0.6 ounces/square yard, and more preferably between about 0.2 to about 0.4 ounces/square yard. If hydrophilic fibers are used, the coating weight should be between about 0.2 to about 1 ounces/square yard, more preferably between about 0.2 to about 0.8 ounces/square yard, and more preferably between about 0.2 to about 0.6 ounces/square yard. If the fibers are a combination of hydrophobic and hydrophilic fibers the same parameters as discussed in connection with the hydrophobic fibers applies.

The plastic polymer microfibers preferably have an average diameter of about 100 microns or less, more preferably between about 1 to about 50 microns, and more preferably have an average diameter of between about 0.5 microns to about 25 microns.

The plastic polymer microfibers described above may also be used to coat release liners 14 or papers 14 used to cover adhesive attachment strips 13 on absorbent products (see FIG. 4). Such release liners take advantage of the same spray technology and provides a release liner with optimum release properties. The melt blown plastic polymer microfibers 13 are sprayed on a paper substrate in a molten state, which delivers a somewhat coarse surface with good release properties without the use of silicone reagents that are currently used in the art. The plastic polymer is as described above, with polyethylene preferred. In certain preferred embodiments, the plastic polymer microfiber coating has a weight of about 1 ounces/square yard and the microfibers have an average diameter of about 100 microns or less. More preferably, the plastic polymer is polyethylene and has a coating weight between about 0.2 to about 1 ounces/square yard; more preferably the coating weight is between about 0.4 to 0.9 ounces/square yard, and more preferably between about 0.65 to 0.80 ounces/square yard, and the microfibers have an average diameter between about 0.5 to about 25 microns. The polymer may also be compounded with the release agents to further improve the release properties of the paper, such as Acrawax C which is a synthetic wax having a melting point between 83° –143° C. Actawax C is used as an anti-tack agent and is available from Lenza Inc.

In another aspect of this invention, absorbent products incorporating the components of the invention are disclosed. In one embodiment of the invention, an absorbent product for adhesive attachment to a wearer's garment is presented (see FIG. 4). This product comprises a liquid impermeable backing 16; a liquid permeable facing 18; and an absorbent core 15 fixed between the backing 16 and facing 18. The backing and/or facing may optionally be coated with pressure-sensitive adhesive microfibers before contacting with the absorbent core 15. The facing, backing, or absorbent core may further have a liquid or odor absorbent immobilized on it.

In another embodiment of the invention, an absorbent product comprising an absorbent core; a liquid impermeable backing; a facing material formed in situ from plastic polymer microfibers; pressure-sensitive adhesive microfiber coating on the side of the backing that is contacted with the wearer's garment, and a release paper, as previously described is disclosed. FIGS. 1 and 4 are illustrative.

In another embodiment, an absorbent product comprising an absorbent core; a facing and backing formed in situ from plastic polymer microfibers; pressure-sensitive adhesive microfiber coating on the side of the backing that is contacted with the wearer's garment; and a release paper, as previously described is disclosed. FIGS. 2 and 4 are illustrative.

The parameters for these absorbent products, such as the particular microfibers used, the coating weight, and size of the microfibers, is as discussed above in connection with the various components of the invention.

The invention is further illustrated in the following examples. These examples are for illustrative purposes only and should not be construed as limiting the appended claims.

EXAMPLES

Example 1

Forming Hydrophobic Fibers

Hydrophobic fibers may be formed from Petrothene low density polyethylene resin NA 601 which has a melt index of 2000. This product is commercially available from USI Corporation. The fibers are formed by spraying the molten material through a spray nozzle at 350° F., at low air consumption.

Example 2

Forming Hydrophilic Fibers

There are two ways to form hydrophilic fibers. The first approach is to spray surface active dispersion on formed thermoplastic fibers. The other is to incorporate surface active agent concentrate into the plastic pellets, DOW XU U1518.15, prior to fiber spray. The surface active pellets are melted and mixed together with the fiber forming plastic. A typical formulation would be:

| Petrothene NA601 | 100 |
|---|---|
| Dow XU 61518.15 | 25 |

The Petrothene is the fiber forming polyethylene which is mixed with Dow surface Active Concentrate.

As in the case of hydrophobic fibers in Example 1, the hydrophilic fibers were formed with a spray nozzle set-up at 350° F. and at a low air consumption.

Example 3

Forming Microfibers and Components Comprising Pressure-Sensitive Adhesives

The sprayed or melt blown pressure-sensitive adhesive microfibers consist of small diameter adhesive fibers having an average diameter not greater than about 100 microns, preferably about 50 microns, and more preferably having a diameter of from about 1–25 microns. These microfibers are made by extruding a molten, pressure-sensitive adhesive through a micro-spray nozzle or through a plurality of fine, usually circular capillaries as filaments into a low velocity gas (e.g., air) stream that attenuates the filaments of the molten pressure-sensitive adhesive material to reduce their diameter to the range stated above. The pressure-sensitive adhesive microfibers are carried by the low velocity gas stream and are deposited on either a facing or backing, which is then brought into contract with an absorbent panel.

The commonly used equipment for fiberization is the well-known melt blown die or the spray nozzle set-up.

Some typical fiber forming hot melt pressure-sensitive adhesives are as follows (the units are parts):

|  | Formula 1 | Formula 2 | Formula 3 |
|---|---|---|---|
| Kraton 1117 | 100 | | |
| Kraton RP 6403 | | 100 | 100 |
| Wingtack Plus | 130 | 130 | 120 |
| Wingtack 10 | | 50 | |
| LIR 310 | | | 50 |
| Butyl Zimate | 2 | 2 | 2 |
| Santovar A | 1 | 1 | 1 |

The Kraton RD 6403 is a Shell SIS (Styrene-isoprene-styrene) thermoplastic rubber having 42% coupling efficiency and 220,000 M.W. It has 17% styrene.

The Kraton 1117 is a commercially available thermoplastic rubber having 65% coupling efficiency and 17% styrene.

Wingtack Plus is a solid hydrocarbon resin supplied by Goodyear Chemical Company and used as a tackifier for thermoplastic rubber. It has a softening point of 95° C.

Wingtack 10 is a liquid hydrocarbon resin and is used as a plasticizer. It has a softening point of 10° C.

LIR 310 is a liquid SI polymer available commercially from Kuraray Chemical Company, and it is used in the formulation as a plasticizer.

The plastic polymer microfibers may be prepared using the same equipment. Examples 1 and 2 are illustrative of plastic polymer microfiber formulations.

Example 4

Components Coated with Pressure-Sensitive Adhesives for Adhering Liquid or Odor Absorbents A typical pressure-sensitive adhesive formulation which can be formed into a microfiber and which will have high adherence to the odor or liquid absorbent powder:

| Kraton 1117 | 100 |
|---|---|
| Wingtack Plus | 130 |
| Butyl Zimate | 2 |
| Santovar A | 1 |

The Kraton is a thermoplastic rubber which gives the internal strength to the pressure-sensitive adhesive.

The Wingtack Plus is a hydrocarbon tackifier to give the adhesive tack properties.

Both Butyl Zimate and Santovar A are antioxidants for improved aging stability.

Example 5

Polyethylene Release Surface

A low density polyethylene resin available from USI, Petrothene NA 601, has been successfully formed into molten fibers and deposited onto paper surface using the molten fiber spray technology discussed in Example 1.

Example 6

Modified Polyethylene Release Surface

The polyethylene from Example 5 can be modified with a high melting wax before fiberization like Actawax C. An addition of 2–5% of the wax before fiberization will further enhance the release properties.

Example 7

Pressure-Sensitive Adhesive Microfibers Formed Without Plasticizer

| Kraton 1117 | 100 |
|---|---|
| Wingtack Plus | 130 |
| Butyl Zimate | 2 |
| Santovar A | 1 |

The Kraton Rubber is tackified with Wingtack Plus and stabilized with two antioxidants; Butyl Zimate and Santovar A.

Example 8

Plasticized Pressure-Sensitive Adhesive Microfiber Compositions

| Kraton 1117 | 100 |
|---|---|
| Wingtack Plus | 130 |
| Wingtack 10 | 50 |
| Santovar A | 2 |
| Butyl Zimate | 1 |
| Kraton 1112 | 100 |
| Arizona 7115 L | 120 |
| Exxon ECR 143 H | 40 |
| Butyl Zimate | 2 |
| Santovar A | 1 |

The plasticized formulations are plasticized with liquid Wingtack 10 resin and Exxon ECR 143H resin. Exxon ECR 143H is a light color hydrogenated aliphatic resin. It has a softening point of 12° C. and a viscosity of 4212 cps at 50° C. and an average molecular weight of 462. It is available from Exxon Chemical Co. They could also be plasticized with liquid elastomers. Arizona 7115 L is a terpene based tackifier with a softening point of about 115° C. It is available from Arizona Chemical Co. Kraton 1112 is a styrene-isoprene (SI) polymer believed to be about 14% styrene, 86% isoprene, and 40% di-block (SI). It has a melt index of about 23° C. and is available from Shell Chemical Co.

What is claimed is:

1. An absorbent product for adhesive attachment to a wearer's garment comprising:
   a) a liquid impermeable backing;
   b) a liquid permeable facing;
   c) an absorbent core fixed between said facing and backing;
   d) pressure-sensitive adhesive microfiber coating on a garment facing surface of said backing that contacts said wearer's garment;

e) release paper covering, wherein said release paper is a paper coated with microfibers of a plastic polymer, wherein said plastic polymer is selected from the group consisting of polyethylene, polypropylene, ethylene vinylacetate, copolyesters, and plastic and thermoplastic rubber alloys.

2. The absorbent product of claim 1 wherein said facing is further coated with pressure-sensitive adhesive microfibers on the side of the facing that is in contact with the absorbent core, said pressure-sensitive adhesive microfiber coating has a weight of about 0.25 ounces/square yard.

3. The absorbent product of claim 1 wherein said facing is further coated with pressure-sensitive adhesive microfibers on the side of the facing that is in contact with the absorbent core, said pressure-sensitive adhesive microfiber coating has a weight of between about 0.3 to about 0.6 ounces/square yard, and said facing further has a liquid or odor absorbent immobilized on it.

4. The absorbent product of claim 1 wherein said backing is further coated with pressure-sensitive adhesive microfibers on the side of the facing that is in contact with the absorbent core, said pressure-sensitive adhesive microfiber coating has a weight of between about 0.3 to about 0.6 ounces/square yard, and said backing further has a liquid or odor absorbent immobilized on it.

5. An absorbent product for adhesive attachment to a wearer's garment comprising:

a) an absorbent core coated on one side with plastic polymer microfibers, wherein said plastic polymer is selected from the group consisting of polyethylene, polypropylene, ethylene vinylacetate, copolyesters, and plastic and thermoplastic rubber alloys, and said plastic polymer microfibers have a coating weight between about 0.2 to about 0.8 ounces/square yard; and said plastic polymer microfibers have a diameter between about 0.5 to about 25 microns;

b) a liquid impermeable backing secured to said core on the side opposite the side coated with plastic polymer microfibers;

c) pressure-sensitive adhesive microfiber coating on a garment facing surface of said backing that contacts said wearer's garment, wherein said pressure-sensitive adhesive microfibers have a coating weight of about 0.2 to about 0.4 ounces/square yard, and said pressure-sensitive adhesive microfibers have an average diameter of less than about 50 microns;

d) release paper covering, wherein said release paper is a paper coated with microfibers of a plastic polymer, wherein said plastic polymer is selected from the group consisting of polyethylene, polypropylene, ethylene vinylacetate, copolyesters, and plastic and thermoplastic rubber alloys.

6. An absorbent product for adhesive attachment to a wearer's garment comprising:

a) an absorbent core coated on both sides with plastic polymer microfibers, wherein said plastic polymer is selected from the group consisting of polyethylene, polypropylene, ethylene vinylacetate, copolyesters, and plastic and thermoplastic rubber alloys; and said plastic polymer microfibers have a coating weight between about 0.2 to about 0.8 ounces/square yard; and said plastic polymer microfibers have a diameter between about 1 to about 25 microns;

b) pressure-sensitive adhesive microfiber coating on the surface of said backing that is contacted with said wearer's garment, wherein said pressure-sensitive adhesive microfibers have a coating weight of about 0.2 to about 0.4 ounces/square yard; and said pressure-sensitive adhesive microfibers have an average diameter of less than about 50 microns;

c) release paper covering, wherein said release paper is a paper coated with microfibers of a plastic polymer, wherein said plastic polymer is selected from the group consisting of polyethylene, polypropylene, ethylene vinylacetate, copolyesters, and plastic and thermoplastic rubber alloys.

* * * * *